United States Patent [19]

Maeda et al.

[11] 4,271,079
[45] Jun. 2, 1981

[54] 5-(2,5-DIOXOTETRAHYDROFURYL)-3-METHYL-3-CYCLOHEXENE-1,2-DICARBOXYLIC ANHYDRIDE

[75] Inventors: Hiroshi Maeda; Nagao Ariga; Hiroshi Oikawa; Hidemitsu Tominaga, all of Chiba, Japan

[73] Assignee: Dainippon Ink & Chemicals, Inc., Tokyo, Japan

[21] Appl. No.: 72,642

[22] Filed: Sep. 5, 1979

[30] Foreign Application Priority Data

Sep. 7, 1978 [JP] Japan .................. 53-109115
Jul. 26, 1979 [JP] Japan .................. 54-94307

[51] Int. Cl.³ .......................... C07D 307/89
[52] U.S. Cl. .................. 260/346.3; 260/346.6; 528/87; 528/353
[58] Field of Search .............. 260/346.3, 346.6

[56] References Cited

U.S. PATENT DOCUMENTS 3,264,261  8/1966  Stark ................ 260/346.3 X
3,391,223  7/1968  Di Leone ............ 260/346.6 X

FOREIGN PATENT DOCUMENTS 52-23669  6/1977  Japan .

Primary Examiner—Richard Raymond
Attorney, Agent, or Firm—Sherman & Shalloway

[57] ABSTRACT

A novel compound, 5-(2,5-dioxotetrahydrofuryl)-3-methyl-3-cyclohexene-1,2-dicarboxylic anhydride, of the following formula is provided.

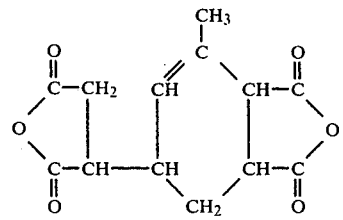

This novel tetracarboxylic acid dianhydride is useful as a curing agent for epoxy resins.

1 Claim, No Drawings

5-(2,5-DIOXOTETRAHYDROFURYL)-3-METHYL-3-CYCLOHEXENE-1,2-DICARBOXYLIC ANHYDRIDE

This invention relates to a novel compound, 5-(2,5-dioxatetrahydrofuryl)-3-methyl-3-cyclohexene-1,2-dicarboxylic anhydride, of the following formula, and an epoxy resin composition containing said novel compound.

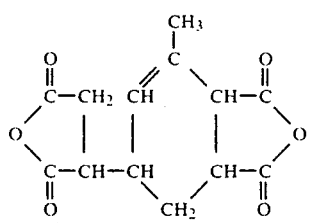

Generally, tetracarboxylic acid dianhydrides of this series are useful not only as raw materials for thermally stable polyimide resins and raw materials for plasticizers for vinyl chloride polymers, but also as raw materials for water-soluble polyesters, and their area of utility is very wide and diversified.

Pyromellitic dianhydride, and benzophenonetetracarboxylic dianhydride, for example, have been widely used heretofore as such tetracarboxylic acid dianhydrides. However, since these aromatic tetracarboxylic acid dianhydride have a high melting point and are highly reactive, their handleability and processability are not satisfactory. Also, these materials are expensive. The use of these aromatic tetracarboxylic acid dianhydrides are therefore limited.

For example, when such an aromatic tetracarboxylic dianhydride as described above is used as a curing agent for an epoxy resin, its compatibility with the epoxy resin is poor, and the curing reaction begins simultaneously with the melting of the resin. Accordingly, the pot life of the epoxy resin is short. Since such an aromatic tetracarboxylic acid dianhydride alone cannot be used for casting, potting, or encapsulation, it is the current practice to mix it with a dicarboxylic acid anhydride such as maleic anhydride.

It has been desired therefore to develop novel tetracarboxylic acid dianhydrides having low melting points and good solubility in various solvents in the fields in which the aromatic tetracarboxylic dianhydrides are used.

The present inventors noted the unique reactivity of 3-methyl-4-cyclohexene-1,2-dicarboxylic anhydride (to be abbreviated PMAA) of the following formula

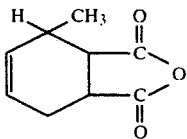

and extensively investigated compounds derived from PMAA. These investigations led to the discovery that the tetracarboxylic acid dianhydride of formula (I) can be prepared from PMAA and maleic anhydride by a very simple operation. The present inventors also found that mixing of the tetracarboxylic acid dianhydride of formula (I) with an epoxy resin yields a thermosetting resin composition having the various characteristics to be described as well as a high heat distortion temperature (measured in accordance with ASTM D-648) which is one measure for the thermal stability of a cured resin.

Thus, the present invention provides 5-(2,5-dioxotetrahydrofuryl)-3-methyl-3-cyclohexene-1,2-dicarboxylic anhydride (to be abbreviated MCTC), which is an aliphatic tetracarboxylic acid dianhydride having good solubility in various solvents and a lower melting point than the aforesaid conventional aromatic tetracarboxylic dianhydrides, and a thermosetting epoxy resin composition having superior thermal stability, consisting essentially of an epoxy resin (to be referred to as component A), and MCTC (to be referred to as component B).

MCTC of formula (I) can be prepared by charging a reactor with PMAA of formula (II) and 0.2 to 5 moles, per mole of MCTC, of maleic anhydride, heating the mixture with stirring at a temperature of 160° to 220° C. for 2 to 24 hours in the presence or absence of a catalyst, removing the unreacted materials by vacuum distillation, dissolving the resulting crude product in acetic anhydride or a ketone such as methyl isobutyl ketone, and recrystallizing it.

In this process, the reaction between PMAA and maleic anhydride proceeds via an addition reaction between PMAA as a hydrogen donor and maleic anhydride as a hydrogen acceptor (also called "ene synthesis") by the mechanism schematically shown below. At this time, transfer of the double bond and the formation of an intercarbon linkage occur simultaneously. A general example of "ene synthesis" is described, for example, in Alder, H. von Brachel: Ann., 651, 141 (1962).

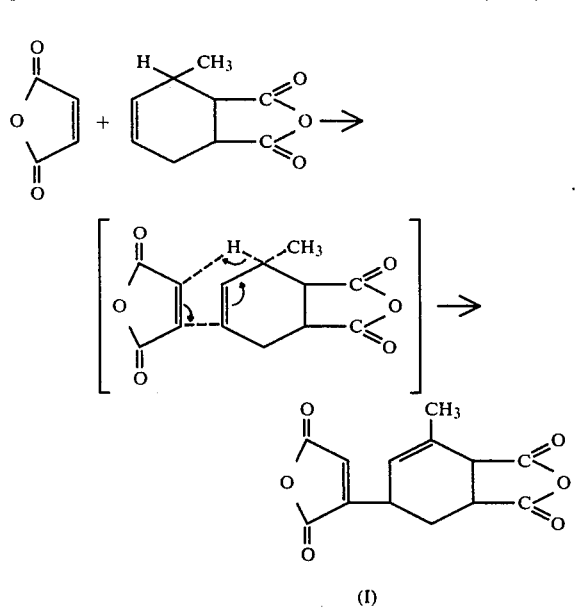

Known methods for ene synthesis, such as a method using a halogen (e.g., bromine) as a catalyst (see Japanese Patent Publication No. 23669/77), and a method using ortho-dichlorobenzene as a solvent [see Org. Synth., IV, 766 (1963)], can be applied to the production of 5-(2,5-dioxotetrahydrofuryl)-3-methyl-3-cyclohexene-1,2-dicarboxylic anhydride by reacting PMAA with maleic acid at a high temperature.

The resulting MCTC is a normally white crystal having a molecular weight of 264, an acid anhydride equivalent of 132 and a melting point of 167.5 to 168.5 (determined by a capillary method), and is useful as a curing agent for thermally stable epoxy resins, or as a raw material for thermally stable resins such as polyesters, polyamides or polyimides.

For example, when MCTC is used as a curing agent for a liquid epoxy resin, its compatibility with the epoxy resin is good, and the resulting epoxy resin composition can be fabricated by casting, potting or encapsulation. As will be clearly seen from a comparison of Examples 2 and 4 with Comparative Examples 1, 2 and 3 to be given hereinbelow, MCTC has better workability than known aromatic tetracarboxylic acid dianhydrides and cured cast articles obtained by using MCTC have a high heat distortion temperature, and exhibit thermal stability equivalent to or higher than cured cast articles prepared from a mixture of benzophenonetetracarboxylic dianhydride and maleic anhydride used as a control.

In other fields of application of MCTC, heating of MCTC with a diamino compound in dimethyl formamide or dimethylsulfoxide as a solvent with stirring yields a polyamide corresponding to the diamino compound. Heating of this polyamide at a temperature of at least 200° C. gives a polyimide. Examples of the diamino compounds include aromatic diamino such as diaminodiphenylsulfone, diaminodiphenylmethane and phenylenediamine, and aliphatic diamino compounds such as ethylenediamine and hexamethylenediamine. The polyamides and polyimides obtained are useful as thermally stable resins.

Products obtained by curing epoxy resins, as is well known, are used in a wide range of applications including potted or encapsulated electrical devices, impregnated articles, coated articles, laminated boards, and adhesives. These articles all require heat resistance or thermal stability, and this requirement has been increasingly stronger in recent years with a great advance in technology relating to electronics and transportation.

As is well known, too, the properties of these articles depend upon the properties of the cured articles, specifically the properties attributed to the chemical structures of the epoxy resin and a curing agent therefor which are the major constituents of the cured articles.

The thermal stability of a cured epoxy resin article also depends to a large extent upon the chemical structures of the two components. Particularly, the crosslinking density of the resin within the molecules is important, and it is known that the heat resistant temperature of the cured article becomes higher as the crosslinking density is larger.

Thus, investigations are also under way about curing agents for epoxy resins, and various curing agents for thermally stable epoxy resins have been developed. Pyromellitic anhydride and benzophenonetetracarboxylic anhydride are generally known as such thermally stable curing agents. However, these aromatic tetracarboxylic acid dianhydrides have a melting point of more than 200° C. and high reactivity. Furthermore, their compatibility with epoxy resins is poor, and it is necessary to mix them at high temperatures. Since the curing reaction proceeds simultaneously with the melting, the pot life of the resin is short. Accordingly, such an aromatic tetracarboxylic acid dianhydride, when used alone, has the defect that it is difficult to use in casting, potting, encapsulating or lamination or as an impregnating varnish.

Thus, such an aromatic tetracarboxylic acid dianhydride is generally used in combination of with a dibasic acid dianhydride such as maleic anhydride, and as a result, the thermal stability of the resin is impaired.

In contrast, when in accordance with the present invention, MCTC is used as a curing agent for epoxy resins, all of the defects of the conventional curing agents can be removed.

The epoxy resin, component (A), which constitutes the epoxy resin composition of this invention may be any compound which contain at least one epoxy group in the molecules. Typical examples include glycidyl ethers of diphenol such as 2,2'-bis(4-hydroxyphenyl)propane and 2,2'-bis(4-hydroxy-2,6-dibromophenyl)-propane; polyglycidyl ethers of polyphenols such as a condensate between formaldehyde and phenol or cresol (novolak resin); di- or poly-glycidyl ethers of diols or polyols such as 1,4-butanediol, diethylene glycol, dipropylene glycol, glycerol, trimethylolpropane, pentaerythritol, and 2,2'-bis(4-hydroxycyclohexyl)propane; di- or polyglycidyl esters of di- or polycarboxylic acids such as phthalic acid, terephthalic acid, isophthalic acid, (methyl)hexahydrophthalic anhydride, (methyl)-tetrahydrophthalic anhydride and trimellitic acid; triglycidyl esters of cyanuric acid or isocyanuric acid; di- or polyglycidylamines such as diglycidyl phenylamine and 4,4'-bis(diglycidylamino)diphenylmethane; epoxidized polybutadienes; alicyclic epoxy compounds such as vinylcyclohexene dioxide, dicyclopentadiene dioxide, 1-(1-methyl-1,2-epoxyethyl)-3,4-epoxymethylcyclohexane, 3,4-epoxycyclohexylmethyl-3,4-epoxycyclohexanecarboxylate, bis(3,4-epoxycyclohexylmethyl)phthalate, dipentene dioxide, diethyleneglycol-bis(3,4-epoxy-cyclohexene carboxylate), 3,4-epoxy-hexahydrobenzal-3,4-epoxycyclohexane-1,1-dimethanol and ethyleneglycol-bis(3,4-epoxytetrahydro-dicyclopentadiene-8-yl) ether; epoxidized polyunsaturated compounds such as an epoxidized product of a diester obtained from 2,7-octadienol or 1,7-octadienol and phthalic anhydride or hexahydrophthalic acid; diglycidyl ethers obtained, as described in Japanese Patent Publication No. 7788/67, by hydrogenating the aromatic ring of a diglycidyl ether of 2,2'-bis(4-hydroxyphenyl)propane or 2,2'-bis(2-hydroxyphenyl)methane in the presence of a catalyst such as rhodium or ruthenium to convert it to an aliphatic ring; diglycidyl ethers obtained by reacting an alcoholic dihydroxy compound with epichlorohydrin in the presence of an acid catalyst such as $BF_3$, the dihydroxy compound being prepared by addition reaction between 2,2'-bis(2-hydroxyphenyl)methane and ethylene oxide or propylene oxide, and then dehydrochlorinatingly cyclizing the product; and monoepoxide compounds such as butyl glycidyl ether, phenyl glycidyl ether, p-secbutylphenyl glycidyl ether and cresyl glycidyl ether. Of these, the di- or polyglycidyl ethers of diphenols or polyphenols, di- or polyglycidylamines, and alicyclic epoxy compounds are preferred in affording resin composition having superior thermal stability.

The other compound (B), i.e. MCTC, which constitutes the epoxy resin composition of this invention is obtained by the method described hereinabove. The mixing ratio between the epoxy resin (A) and the MCTC (B) is such that the resulting composition contains 0.6 to 1.2 carboxylic anhydride groups, preferably 0.8 to 1.0, carboxylic anhydride group, per epoxy group.

The composition of this invention may contain plasticizers or non-reactive diluents such as dibutyl phthalate, dioctyl phthalate and tricresyl phosphate, and non-reactive solvents such as acetone, methyl ethyl ketone and dimethylformamide. If required, it may contain other additives. Examples of the other additives include fillers such as asphalt, quartz powder, mica, glass fibers, cellulose, talc, clay, kaolin, bentonite, calcium carbonate, alumina hydrate, metallic powder (such as aluminum powder), pigments, dyes, molding lubricants, fire retardants, and other modifying agents.

To ensure sufficient curing, conventional curing promotors may be incorporated into the resin composition of this invention. Examples of the curing promotors are amines such as triethylamine, N-benzyldimethylamine, triethanolamine, N-dimethylaniline, tris(dimethylaminomethyl)phenol and diazabicycloundecene; amine salts such as $BF_3$-monoethylamine; imidazoles such as 2-ethyl-4-methylimidazole; and metal alcoholates such as sodium alcoholate.

The epoxy resin of this invention has various advantages. Specifically, MCTC has a low melting point and low reactivity and has good compatibility with an epoxy resin as compared with a composition comprising a known tetracarboxylic acid dianhydride such as pyromellitic anhydride or benzophenonetetracarboxylic anhydride instead of MCTC. Thus, the operation of mixing MCTC with the epoxy resin is very easy, and the composition has storage stability over a long period of time. Accordingly, while cast articles including an inorganic filler such as quartz powder or a laminated board by a prepreg technique are extremely difficult to produce from a composition containing a known tetracarboxylic acid dianhydride, these products can be very easily produced from the epoxy resin composition of this invention. Furthermore, molded products or coated films from the epoxy resin composition of this invention show superior thermal stability, mechanical properties, electrical properties and chemical resistance.

The epoxy resin composition of this invention, if desired, containing the various additives exemplified hereinabove, are used not only in casting, potting or encapsulation, but also in impregnation, lamination, bonding, coating, etc.

The following Examples and Comparative Examples illustrate the present invention more specifically. In these examples, all parts and percentages are by weight unless otherwise specified.

REFERENCE EXAMPLE (preparation of starting PMAA)

The inside of a reactor equipped with a thermometer, a condenser and a stirring rod was purged with an inert gas, and it was charged with 98.1 parts of maleic anhydride and 49 parts of benzene. Then, while maintaining the temperature of the inside of the reactor at 40° to 45° C., 192.4 parts of a hydrocarbon mixture of the following composition was added over the course of 1 hour.

| | Composition of the hydrocarbon mixture (%) |
|---|---|
| Pentene-1 | 0.20 |
| 2-Methyl-butene-2 | 1.32 |
| 2-Methyl-pentane | 2.70 |
| 3-Methyl-pentane | 0.10 |
| n-Hexane | 0.22 |
| Cyclopentane | 6.34 |
| Cyclopentene | 18.21 |
| trans-1,3-Pentadiene | 46.57 |
| cis-1,3-Pentadiene | 23.18 |
| Cyclopentadiene | 0.49 |
| Dicyclopentadiene | 0.01 |
| Other compounds | 0.66 |
| Total | 100.00 |

After the addition, the mixture was stirred at 45° C. for 4 hours. After confirming that maleic anhydride was consumed, the hydrocarbon mixture and the solvent in the reactor were recovered by distillation.

Thus, 165 parts (yield 99%) of the desired 3-methyl-4-cyclohexene-1,2-dicarboxylic anhydride (PMAA) was obtained.

EXAMPLE 1

Preparation of the tetracarboxylic acid dianhydride of the invention:

A reactor equipped with a condenser was charged with 45.8 parts of PMAA obtained in the Reference Example and 54.2 parts of maleic anhydride (PMAA/maleic anhydride molar ratio=$\frac{1}{2}$), and the mixture was stirred at 200° C. for 4 hours.

Then, the unreacted PMAA and maleic anhydride were recovered by vacuum distillation. The distillation was performed until finally the pressure became 10 mmHg and the temperature of the still reached 200° C.

As a result, 33.7 parts of unreacted PMAA and 44.8 parts of unreacted maleic anhydride were recovered.

Then, 21.5 parts of the crude product remaining in the reactor was taken out, and dissolved in 60 parts of methyl isobutyl ketone at 110° C. The solution was cooled to room temperature to afford 12.3 parts of the tetracarboxylic acid dianhydride of the invention as white crystals having a melting point of 167.5° to 168.5° C.

The product recrystallized from methyl isobutyl ketone was analyzed, and the results are shown in Table 1.

TABLE 1

| Item of analysis | Analytical data | Calculated values |
|---|---|---|
| IR Spectrum | $>C=O$ 1770–80 cm$^{-1}$<br>1850 cm$^{-1}$ | |

TABLE 1-continued

| NMR spectrum | Chemical shift (ppm) | | Corresponding number of protons |
|---|---|---|---|
| | $\delta$—$CH_3$ | 1.9 | 3 |
| | $\delta$>$CH_3$ (cyclohexene ring) | | |
| | $\delta$=$CH$ (cyclohexene ring) | 2.5– | 6 |
| | $\delta$—$CO$—$CH_2$— (succinyl) | 3.4 | |
| | $\delta$—$COCH$< (succinyl) | | |
| | $\delta$—$CO$—$CH$< (cyclohexene ring) | 3.8 | 2 |
| | $\delta$>$C$=$CH$— (cyclohexene ring) | 5.6 | 1 |
| Molecular weight (millimass method) | 264.062 ± 0.002 | | (Calculated: 264.063 for $^{12}C_{13}{}^1H_{12}{}^{16}O_6$) |
| Neutralization equivalent | 64.2 | | (Calculated: 66.1) |
| Iodine value (Wijs method) | 93.7 | | (Calculated: 96.1) |
| Melting point (capillary method) | 167.5 to 168.5° C. | | |
| Elemental analysis | C:58.66; H:4.66; O:36.68 | | Calculated C:59.09; H:4.58 O:36.33 |

From the results of these analyses, especially those obtained with the NMR spectrum including the value of the chemical shift of the methyl group, the absence of a microstructure of the absorption of hydrogen attached to the methyl group, and the number of protons bonded to the double bond, it was ascertained that as a result of ene synthesis, the double bond of the cyclohexene ring moved from the 4-position of PMAA to the 3-position of the reaction product. Furthermore, from the molecular weight, the neutralization equivalent, the iodine value and the results of elemental analysis, the white crystalline product obtained in this example was determined to have the structure of formula (I).

EXAMPLE 2

Preparation of an epoxy resin composition using the tetracarboxylic acid dianhydride of this invention:

Fifty-five parts of the tetracarboxylic acid anhydride MCTC obtained in Example 1 and 100 parts of Epiclon 850 (a trademark for a liquid epoxy resin having an epoxy equivalent of 192, reproduced by Dainippon Ink and Chemicals, Inc.) were mixed at 170° C. for 20 minutes. The mixture was cooled to 80° C., and then 0.3 part of dimethylbenzylamine was added. The mixture was cast into a mold, and cured under heat. Then, the heat distortion temperature of the product was measured.

The heat curing conditions and the heat distortion temperature measured are shown in Table 2.

The composition of the above recipe was poured into a test tube, and heated over an oil bath at 100° C. Thus, the gel time of the composition was measured. The results are also shown in Table 2.

The gel time denotes the time which elapses from the beginning of heating the composition at 100° C. until the flowability of the composition disappears.

EXAMPLE 3

Preparation of an epoxy resin composition using the tetracarboxylic dianhydride of this invention:

The same procedure as in Example 2 was repeated except that the amount of MCTC was changed to 62 parts, and the curing was effected first at 160° C. for 15 hours and then at 220° C. for 24 hours. The gel time at 100° C. of the composition was measured, and then, the heat distortion temperature, flexural strength, weight loss on heating, dielectric constant, dielectric tangent, volume inherent resistivity and tracking resistance of the resulting cured cast article were measured. The results are shown in Table 3.

COMPARATIVE EXAMPLE 1

Test for the suitability of a commercially available tetracarboxylic acid dianhydride as a curing agent for epoxy resins:

One hundred parts of Epiclon 850 was mixed with 50 parts of a commercially available benzophenonetetracarboxylic dianhydride (molecular weight 322) used as a curing agent for thermally stable epoxy resins at 170° C. When the composition was cast in the same way as in Example 2, it was gelled soon after the resin and the curing agents were completely mixed.

COMPARATIVE EXAMPLE 2

Test for the suitability of the commercially available tetracarboxylic acid dianhydride as a curing agent for epoxy resins:

The same procedures as in Examples 2 and 3 were repeated except that 31 parts of the benzophenonetetracarboxylic acid dianhydride used in Comparative Example 1, 19 parts of maleic anhydride and 100 parts of Epiclon 850 were used. The gel time at 100° C. of the composition, and the heat distortion temperature, flexural strength, weight loss on heating, dielectric constant, dielectric tangent, volume inherent resistivity and tracking resistance of the resulting cured cast article were measured, and the results are shown in Tables 2 and 3.

EXAMPLE 4

Preparation of an epoxy resin composition using the tetracarboxylic acid anhydride of the invention:

The procedure of Example 2 was repeated except that a mixture composed of 50 parts of Epiclon 850, 50 parts of Epiclon N-740 (a trademark for a novolak-type epoxy resin having an epoxy equivalent of 188, made by Dainippon Ink and Chemicals, Inc.) and 48.6 parts of MCTC obtained in Example 1 was used, and dimethylbenzylamine was not used. The heat distortion temperature of the cured cast article, and the gel time at 100° C. of the resin composition were measured. The results are shown in Table 2.

COMPARATIVE EXAMPLE 3

Test for the suitability of the a commercially available tetracarboxylic acid dianhydride as a curing agent for epoxy resins:

The same procedure as in Example 2 was repeated except that 32 parts of the benzophenonetetracarboxylic acid dianhydride used in Comparative Example 1, 19 parts of maleic anhydride, 50 parts of Epiclon 850, and 75 parts of Epiclon N-740 were used. However, the composition was gelled before the resin and the curing agent got mixed. Thus, casting of the composition was impossible.

TABLE 2

|  |  | Example 2 | Example 4 | Comparative Example 2 |
|---|---|---|---|---|
| Gel time at 100° C. (minutes) |  | 20 | 30 | 10 |
| Heat distortion temperature (°C.) | Curing conditions |  |  |  |
|  | 160° C. × 15 hours | 194 | 221 | 213 |
|  | 160° C. × 15 hours + 200° C. × 15 hours | 225 | 243 | 243 |
|  | 160° C. × 15 hours + 220° C. × 15 hours | 266 | 260 | 260 |
|  | 160° C. × 15 hours + 240° C. × 15 hours | 246 | 246 | 246 |

TABLE 3

| Test items |  | Example 3 | Comparative Example 2 |
|---|---|---|---|
| Gel time (minutes) |  | 19 | 10 |
| Heat distortion temperature (°C.) |  | 275 | 260 |
| Tensile strength at room temperature (kg/mm$^2$) |  | 3.1 | 2.8 |
| Flexural strength (kg/mm$^2$) | Room temperature | 7.7 | 5.8 |
|  | 150° C. | 5.4 | 4.7 |
| Weight loss (%) on heating at 230° C. | after 7 days | 2.8 | 2.8 |
|  | after 28 days | 5.5 | 6.7 |
| Dielectric constant (1 KHz) | Room temperature | 3.4 | 3.4 |
|  | 150° C. | 3.6 | 3.6 |
| Dielectric tangent (%) (1 KHz) | Room temperature | 0.9 | 0.9 |
|  | 150° C. | 0.6 | 0.6 |
| Volume inherent resistivity (ohms-cm) | Room temperature | 1 × 10$^{16}$ | 1 × 10$^{16}$ |
|  | 200° C. | 1 × 10$^{12}$ | 1 × 10$^{12}$ |
| Tracking resistance (*1) |  | more than 101 cycles; 1.3 mm (at the 101st cycle) | 4 cycles |

(*1): Tracking resistance

The test was conducted at an applied voltage of 380 V and an interrupting current of 0.5 A in accordance with IEC (International Electrical Commission) and DIN (West German Industrial Standards). The number of test cycles until breakage is determined. When the test can be performed through at least 101 cycles, the depth of penetration is determined.

EXAMPLE 5

Preparation of an epoxy resin composition using the tetracarboxylic acid dianhydride of the invention:

The procedure of Example 3 was repeated except that Epiclon 850 was changed to Epiclon 830 (a trademark for a diglycidyl ether of bisphenol F having an epoxy equivalent of 180, made by Dainippon Ink and Chemicals, Inc.), and the amount of MCTC was changed to 67 parts. The heat distortion temperature and the gel time at 100° C. were measured. The results are shown in Table 4.

EXAMPLE 6

Preparation of an epoxy resin composition using the tetracarboxylic acid dianhydride of the invention:

The same procedure as in Example 3 was repeated except that 50 parts of Epiclon N-740, 50 parts of Epiclon 850, and 63 parts of MCTC were used. The heat distortion temperature and the gel time at 100° C. were measured, and the results are shown in Table 4.

EXAMPLE 7

Preparation of an epoxy resin composition using the tetracarboxylic acid dianhydride of the invention:

The same procedure as in Example 3 was repeated except that 50 parts of Epiclon 850, 50 parts of ERL-4221 (a trademark for an alicyclic epoxy resin having an epoxy equivalent of 140, made by Union Carbide Corporation) and 73 parts of MCTC were used. The heat distortion temperature, and the gel time at 100° C. were measured, and the results are shown in Table 4.

EXAMPLE 8

Preparation of an epoxy resin composition using the tetracarboxylic acid anhydride of the invention:

The same procedure as in Example 3 was repeated except that 50 parts of Epiclon 850, Epiclon 430 (a trademark for a glycidylamine-type epoxy resin having an epoxy equivalent of 112, made by Dainippon Ink and Chemicals, Inc.), and 84 parts of MCTC were used. The heat distortion temperature and the gel time at 100° C. were measured, and the results are shown in Table 4.

TABLE 4

| Example | Epoxy resins | Heat distortion temperature (°C.) | Gel time (minutes) |
|---|---|---|---|
| 5 | Epiclon 850 | 273 | 23 |
| 6 | Epiclon 850/Epiclon N-740 | 276 | 16 |
| 7 | Epiclon 850/ERL-4221 | 285 | 13 |
| 8 | Epiclon 850/Epiclon 430 | 291 | 15 |

EXAMPLE 9

Preparation of an epoxy resin composition of the invention:

A flask equipped with a condenser was charged with 62 parts of MCTC and 100 parts of Epiclon 850, and they were mixed at 170° C. for 20 minutes. The epoxy equivalent of the mixture became 378.

The temperature of the mixture was lowered to 100° C., and 133 parts of acetone was added. The mixture was cooled to room temperature, and then 0.1 part of benzylmethylamine was added to form a composition having a viscosity, at 25° C., of 11.0 centipoises.

When this composition was stored for one month at 25° C., its viscosity was 11.2 centipoises, showing scarcely any change. It is seen from the result that the composition of this invention has superior storage stability.

APPLICATION EXAMPLE 1

Preparation of a polyimide:

In 100 parts of dimethylformamide were dissolved 24 parts of MCTC obtained in Example 1 and 20 parts of 4,4'-diaminodiphenylsulfone. The solution was stirred at 100° C. for 24 hours to form a dimethylformamide solution of a polyamide. The solution was coated in film form on a glass plate, and heated at 70° C. for 1 hour to remove the dimethylformamide and thereby to form a polyamide film. Then, the film was heated at 220° C. for 1 hour to form a polyimide film. The resulting polyimide film had a glass transition temperature (Tg) of 305° C. In the IR spectrum of this film, a characteristic absorption of the imide linkage was seen at 1760, 1700, 700, and 600 cm$^{-1}$.

APPLICATION EXAMPLE 2

Production of a laminated article:

The composition prepared in Example 9 was impregnated with glass cloths (treated with borane), and dried at room temperature for 60 minutes, and then at 150° C. for 8 minutes to prepare 9 prepregs. They were press-formed by a hot press to form a laminated board having a thickness of 1.6 mm. The press-forming was carried out at a temperature of 160° C. and a pressure of 40 kg/cm$^2$ for a period of 60 minutes.

The resulting laminated board was post-cured at 220° C. for 15 hours, and then its flexural strength and flexural modulus of elasticity were measured. The results are shown in Table 5.

TABLE 5

| Measuring temperature (°C.) | Flexural strength (kg/mm$^2$) | Flexural modulus of elasticity (kg/mm$^2$) |
| --- | --- | --- |
| 23 | 38.5 | 1,540 |
| 150 | 31.7 | 1,460 |
| 200 | 19.5 | 1,312 |
| 260 | 8.2 | 992 |

APPLICATION EXAMPLE 3

Preparation of a coating composition:

MCTC (7.0 parts), 52.5 parts of "Epiclon 3050" (a trademark for a bisphenol-type solid epoxy resin having a medium melting point and an epoxy equivalent of 800, made by Dainippon Ink and Chemicals, Inc.), 40 parts of titanium oxide and 0.5 part of "Modaflow" (a trademark for a flow regulating agent made by Monsanto Company) were kneaded and melted in a kneader, then finely pulverized, and passed through a 150-mesh wire gauze to form a white powder coating composition.

The white powder coating composition was coated on a zinc phosphate-treated steel panel having a thickness of 0.8 mm, and the properties of the coated film were tested. The results are shown in Table 6.

COMPARATIVE APPLICATION EXAMPLE

The same procedure as in Application Example 3 was repeated except that 7.0 parts of pyromellitic anhydride was used instead of MCTC.

In the same way as in Application Example 3, the properties of a coated film were tested. The results are shown in Table 6.

TABLE 6

| Test items | Application Example 3 | Comparative Application Example |
| --- | --- | --- |
| Gloss | 83 | 85 |
| Du Pont impact strength (½ inch, 500g) | >50 cm | >50 cm |
| Erichsen | 9.3mm | 9.2mm |
| Crosscut adhesion test | 100/100 | 100/100 |
| Boiling water resistance (6 hrs.) | No change | Whitening |
| Acid resistance (5% H$_2$SO$_4$, 1 month) | No change | No change |
| Alkali resistance (5% NaOH, 1 month) | No change | No change |
| Salt spray (500 hrs; the peel width of the cut portion) | 0 mm | 0 mm |
| Thermal stability (230° C./2 hrs; ΔE) | 3.75 | 4.32 |

What we claim is:

1. Tetracarboxylic acid dianhydride of the formula:

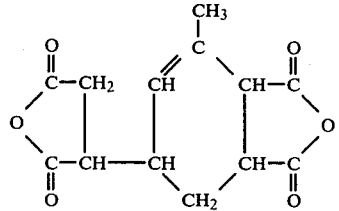

* * * * *